United States Patent [19]
Buytaert et al.

[11] Patent Number: 5,654,555
[45] Date of Patent: Aug. 5, 1997

[54] SYSTEM FOR SUPPLYING A PROCESSED RADIOGRAPHIC IMAGE TO A REMOTE DEVICE

[75] Inventors: Tom Buytaert, Kontich; Lucien Hayen, Antwerp, both of Belgium

[73] Assignee: AGFA-Gevaert, Mortsel, Belgium

[21] Appl. No.: 465,872

[22] Filed: Jun. 6, 1995

[30] Foreign Application Priority Data

Jun. 10, 1994 [EP] European Pat. Off. ............... 94201663

[51] Int. Cl.$^6$ ........................................................ A61B 6/00
[52] U.S. Cl. ............................................. 250/581; 250/583
[58] Field of Search ........................................ 250/581, 582, 250/583, 584; 364/413.13

[56] References Cited

U.S. PATENT DOCUMENTS 4,739,480   4/1988   Oono et al. ............................. 250/584
4,960,994   10/1990  Müller et al. ........................... 378/165

*Primary Examiner*—Michael J. Tokar
*Assistant Examiner*—Kiet T. Nguyen
*Attorney, Agent, or Firm*—Richard J. Birch

[57] ABSTRACT

A system for supplying a processed radiographic image to a remote device. The system is disclosed for supplying a radiographic image obtained by reading an exposed photostimulable phosphor screen that has been processed in a processing station to a remote device such as a display device that is connected with said processing station via a network and a distributed network filing system.

8 Claims, 4 Drawing Sheets

SYSTEM FOR SUPPLYING A PROCESSED RADIOGRAPHIC IMAGE TO A REMOTE DEVICE

BACKGROUND

1. Field of the Invention

The present invention is in the field of digital radiography and relates to a system of supplying a processed radiographic image to a remote station such as a display station, a hard copy recorder, an archiving station etc.

2. Description of the Prior Art

In the field of digital radiography a wide variety of image acquisition techniques have been developed that render a digital representation of a radiation image.

In one of these techniques a radiation image, for example an x-ray image of an object, is stored in a screen comprising a photostimulable phosphor such as one of the phosphors described in European patent publication 503 702 published on Sep. 16, 1992.

In a read out station the stored radiation image is read by scanning the screen with stimulating radiation such as laser light of the appropriate wavelength, detecting the light emitted upon stimulation and converting the emitted light into an electric representation for example by means of an adequately adjusted photomultiplier and finally digitizing the signal.

After readout the residual image left on the photostimulable phosphor screen is erased so that the screen is again available for exposure.

The digital image signal is then processed on-line.

The image is further sent to a processing station where it can be subjected to additional processing steps.

A processing station provides a powerful tool for advanced and interactive image processing. It allows to use the capabilities of the image processing to the fullest extent. Any mistakes regarding image processing that might be introduced during identification of the cassette can be corrected and the image can be re-processed using newly set parameters.

After processing the image can be transmitted to a recorder, e.g. a laser recorder for reproduction on the film size and lay-out of the radiologist's choice and/or it can be transmitted to an archival station.

It is also common practice to display the processed image on a display station for evaluation by a radiologist.

The display station or archival station or recorder to which the processed image is supplied may be positioned in close vicinity of the read out station.

In a hospital environment however, a radiographic image of a patient that is generated in a central radiology room is often reviewed on a location remote from the radiology room.

Typically a radiographic image of a patient is needed in an intensive care unit whereas the image has been recorded in a central radiology room and the read out and processing device is installed in the vicinity of that radiology room.

Instead of printing the image and carrying the hard copy image to the intensive care unit, it is more convenient to transmit the image electronically and to display the transmitted image on a remote display station that is connected with the processing station by a network.

Alternatively the image can be transmitted electronically to a remote recorder for production of a hard copy.

Archiving may also be provided remote from the image processing unit.

The interfacing of an image processing station and a remote station of the above-named kind is generally performed by means of the following two elements: (i) a physical connection between the processing station and the remote station and (ii) a protocol implemented by both systems so as to provide control and interchange of data.

The physical connection can be realized by implementing a local area network (LAN) or a Wide area network (WAN) or by means of a serial or parallel point-to-point connection. A wide variety of suitable physical connections are available on the market: Ethernet (trademark of Xerox corporation), FDDI (Fiber distributed data interchange), RS232, SCSI, etc.

A protocol can be implemented up to different levels of the OSI seven layer model.

Suitable protocols that make data of linked systems accessible in the form of a file or as byte-streams are commercially available for numerous hardware platforms. Examples are: NFS (trademark of Sun Microsystems), TCP-IP, TLI sockets, Netware (trademark of Novell Inc.) etc.

For medical applications dedicated protocols such as ACR-NEMA, DICOM ... or extended protocols such as SPI ... have been developed.

But implementations of these protocols are not yet available for all platforms.

Electronic transmission between devices requires that a common protocol is used so as to enable data interchange, said protocol defining a number of commands that are identically interpreted by either of the systems.

In this particular application however, data are to be transmitted between an image processing unit and one of a great variety of remote display, archival, hard copy ... stations available on the market. All available remote stations do not necessarily use the same protocol.

Therefore arrangements would have to be made with regard to data communication for each individual kind of remote station. This would demand for close cooperation between different parties on the level of hardware, protocols and application software.

European patent application EP 599 097 discloses an X-ray image processing apparatus that allows automatic routing of differently processed versions of an X-ray image to different, selected destinations.

This disclosure does not focus on the communication problems that might be encountered when data are to be transmitted to remote stations of different kinds and no common protocol has been agreed upon.

An additional problem relating to display stations in particular is that each of the number of display devices available on the market have their proper conversion characteristics and their proper limitations.

Hence accurate representation of grey shades may become a problem when an image is converted between an electronic device (e.g. image on disc of the processing station) and a physical medium such as a phosphor in a CRT display device.

OBJECTS OF THE INVENTION

It is an object to provide a system for supplying a processed radiographic image to a remote station such as a display station, hard copy recorder, archival system etc.

It is a further object to provide a system of the above-named kind that is quasi universal, i.e. that enables supplying processed image(s) to many stations of different kinds.

It is a further object to provide such a system for use in connection with a system for reading a radiation image that has been stored in a photostimulable phosphor screen.

It is still a further object to provide such a system wherein display of grey shades is optimized.

Further objects will become apparent from description hereinafter.

STATEMENT OF THE INVENTION

To achieve the above objectives the present invention provides a system for supplying a processed radiation image to a remote station, comprising means for acquiring a digital signal representation of a radiation image, a processing station for processing said digital signal representation, a distributed network system interfacing said processing station and said remote station, data interchange means enabling interchange of data between said processing station and said remote station connected by said network system, storage means accessible by said data interchange means for storing said processed image as a file, means for reading a stored file and for translating the data in the file into a structure suitable for use in an application program running on said remote station.

This invention provides all the necessary tools to transmit fully processed images from the image processing station to any type of remote display station via a distributed network file system, i.e. a general purpose network file system that is implemented by computer vendors on a great number of systems.

In one embodiment said means for acquiring a digital signal representation of a radiation image comprise means for scanning a photostimulable phosphor screen that has been exposed to a radiation image by means of stimulating radiation, means for detecting light emitted upon stimulation, and means for converting the detected light into a digital signal representation.

The radiographic image is generated in the form of a digital signal representation that is then obtained by scanning a photostimulable phosphor screen that has been exposed to penetrating radiation (for example the image of a patient that has been exposed to x-rays) by means of stimulating radiation such as laser light of the appropriate wavelength, detecting the light emitted upon stimulation and converting the detected light into a digital signal representation.

Other acquisition systems that render a digital signal representation of a radiation image may be envisaged such as a system wherein a radiation image is detected by means of a CCD sensor or a selene detector etc.

Also radiographic film scanning systems or systems wherein a digital signal representation of a radiation image is obtained without the use of an intermediate storage medium fall within the scope of the present invention.

The digital signal is then supplied to a processing station where it can be subjected to different kinds of processing executed for different purposes such as gradation processing, contrast enhancement, noise reduction, signal compression etc.

Image processing that can be performed on the read-out image is described in extenso in the following patent applications:

Selection of a diagnostically relevant range: published European patent applications 549 009, 546 600 and European patent application 93 200 376.7; contrast enhancement: published European patent application 527.525 and European patent application 93 200 375.9; noise reduction: European patent application 93 201 432.7.

In one embodiment contrast enhancement is performed in accordance with the following method:

a) the original image is first decomposed into a sequence of detail images at multiple resolution levels and a residual image at a resolution level lower than the minimum of said multiple resolution levels, b) the pixel values of said detail images are then modified to yield pixel values of a set of modified detail images according to at least one non-linear monotonically increasing odd conversion function with a slope that gradually decreases with increasing argument values, and c) finally a processed image is computed by applying a reconstruction algorithm to the residual image and the modified detail images, the reconstruction algorithm being such that if it were applied to the residual image and the detail images without modification, then said original image or a close approximation thereof would be obtained.

Preferably the number of pixels in each detail image decreases at each coarser resolution level.

In one embodiment the detail images at successively coarser resolution levels are obtained as the result of each of K iterations of the following steps:

a) computing an approximation image at a next coarser level by applying a low pass filter to the approximation image corresponding to the current iteration, and subsampling the result in proportion to the reduction in spatial frequency bandwidth, using however the original image as input to said low pass filter in the course of the first iteration;

b) computing a detail image as the pixelwise difference between the approximation image corresponding to the current iteration and the approximation image at a next coarser resolution level computed according the method sub 4.a), both images being brought into register by proper interpolation of the latter image; and wherein the residual image is equal to the approximation image produced by the last iteration.

The processed image is computed by iterating K times the following procedure starting from the coarsest detail image and the residual image:

computing the approximation image at the current resolution level by pixelwise adding the detail image at the same resolution level to the approximation image at the coarser resolution level corresponding to the previous iteration, both images being brought into register by proper interpolation of the latter image, using however the residual image instead of said coarser approximation image in the course of the first iteration.

The modifying function preferably has a slope that gradually decreases with increasing absolute argument values with the exception of the region of lowest absolute argument values where the slope is constant or increasing.

In context of the present invention the remote station can for example be a remotely positioned display station, such as a review station positioned in another location than the processing station.

Such a display station does not only provide the ability to display images but in most cases the display station is equipped with storage capability such as a memory disc and means enabling the running of application software, for example a data base.

Alternative embodiments of remote stations are a hard copy recorder, an archiving station etc.

In this context means for enabling interchange of data between said processing station and said remote station connected by said network system, are means that provide transparent file access among different hardware architectures and operating systems.

The invention requires that a distributed file system is provided. Such file systems are implemented on a great number of general purpose computers, they are not and need not be specific for application in a medical environment.

Suitable data interchange means are systems that make data of linked systems accessible in the form of a file or as byte-streams. Such systems are commercially available for numerous hardware platforms. Examples are: NFS (trademark of Sun Microsystems), TCP-IP, TLI sockets etc.

After processing the image is stored as a file.

One of the advantages of the present invention is that it is indifferent where the storage means are located (which system they are part of) as long as they are accessible through the network and the network file system.

In one embodiment said storage means are part of the processing station. The radiographic image is then stored after processing in a file on said storage means.

In order to display the processed image on the remote display station, the stored file can be copied to an additional storage means of the display station. This file is then retrieved, translated into a format that is interpretable by the application software running on the display station and displayed.

In a particular embodiment more than one remote station can be connected with the processing station through the network system and a processed image can be sent to a predefined remote station.

Means are then provided to associate with a processed image a destination key identifying one of the available remote stations and means are provided to control transmission of an image to the identified remote station.

Such means are described in our European patent application 93200879.0 disclosing a system for displaying a so-called mosaic of radiographic images on one of a plurality of display devices installed in several radiology rooms.

It is also possible that at the identification station a destination is automatically associated with an examination type and examination subtype and a radiologist and that a read out and processed image is automatically transmitted by the processing station or the read out apparatus to the associated destination. This mode of operation is referred to as auto-routing.

The available resolution of the processed image does not always match with the resolution displayable on the display station. Hence in one embodiment means are provided to change the image resolution.

The number of bits per pixel that are available at the output of the processing device is often greater than the number of bits per pixel that can be displayed due to the limited capabilities of display devices. Typically the pixel depth at the output of the processing device is between 12 and 16 bits per pixel whereas commercially available display devices are only capable of displaying 8 to 12 bits per pixel.

A data base or file comprising for each destination a number of configuration data such as pixel depth, pixel resolution, etc. is stored for example in memory provided in the processing station. Upon selection of a destination, the corresponding data are read from the data base or the file and the image is adapted so that its characteristics (pixel depth, resolution etc.) match with the read data.

For example the image resolution can be adapted according to the method disclosed in unpublished European patent application 93200373.4 filed Feb. 11, 1993.

In accordance with this method a digital image representation is decomposed into a sequence of detail images at multiple resolution levels and a residual image, that are stored in a memory device.

The stored images are retrieved up to a specific resolution level so that the processed image after reconstruction (cfr. hereafter) has a resolution that is fits best to the resolution of said display device.

Pixel values of said retrieved detail images are modified to yield pixel values of a set of modified detail images and a processed image is generated by applying a reconstruction algorithm to the residual image and the retrieved and modified detail images, the reconstruction algorithm being such that if it were applied to the residual image and all detail images without modification, then said original image or a close approximation thereof would be obtained.

Image pixels that fall within certain density ranges are not relevant for diagnosis. For example the background information can commonly be disregarded.

In one embodiment of the present invention means are provide to reduce the number of bits per pixel. Said means are either (1) means for disregarding certain density ranges so that only a diagnostically relevant density range is left, said range being such that it can be represented by a number of bits per pixel that is displayable on the display device and/or (2) means for converting the density range or the diagnostically relevant density range onto the displayable density range in an optimal way, namely so that the transmitted image is optimized in accordance with the CRT display characteristics of the remote display station and hence is optimal for making diagnosis on the remote screen. The latter means can be implemented as a look up table representing monitor characteristics.

BRIEF DESCRIPTION OF THE DRAWINGS

Particular aspects of the present invention as well as preferred embodiments thereof will be explained by means of the corresponding drawings wherein.

DESCRIPTION OF THE PREFERRED EMBODIMENTS

A radiation image of an object was recorded on a photostimulable phosphor screen 3 by exposing (radiation emitted by source 2) said screen to x-rays transmitted through the object (not shown). The stimulable phosphor screen 3 was conveyed in a cassette provided with an electrically erasable programmable read only memory 4 (EEPROM) and a galvanic data transmission. A cassette of this kind has been described in U.S. Pat. No. 4,960,994.

The radiation image was first identified in an identification station 5 consisting of a standard PC-based computer with keyboard, monitor and a cassette insertion port.

In this identification station all kinds of data such as patient examination data can be entered via the keyboard.

Alternatively these data can be retrieved from another information system such as a Radiology Information System (RIS).

The identification data were written onto the EEPROM chip on the cassette conveying the photostimulable phosphor screen.

Figure 2:
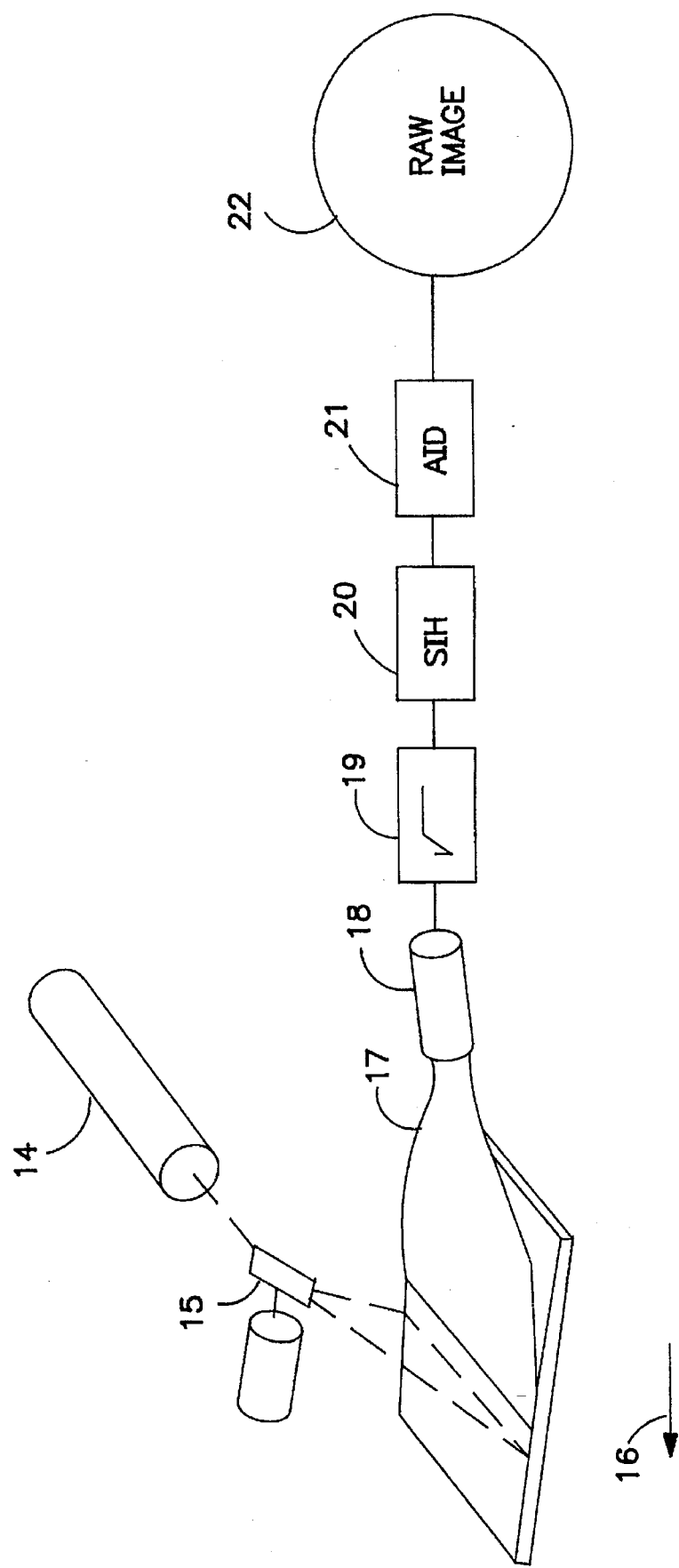
FIG. 2 is a is more detailed view of a system for reading an image stored in a photostimulable phosphor screen.

Then the cassette was fed into a radiation image read-out apparatus 1 where the information stored in the EEPROM and the image stored in the photostimulable phosphor screen were read-out. Image read out is illustrated in FIG. 2. The stored image was read-out by scanning the phosphor screen with stimulating rays emitted by a laser 14. The stimulating rays were deflected into the main scanning direction by means of galvanometric deflection 15. The sub-scanning was performed by transporting the phosphor screen in the sub-scanning direction indicated by arrow 16. The stimulated emission was directed by means of a light collector 17 onto a photomultiplier 18 for conversion into an electrical image representation. Next, the signal was amplified by a square root amplifier 19, sampled by a sample and hold circuit 20, and converted into a 12 bit signal by means of an analog to digital converter 21.

Figure 1:
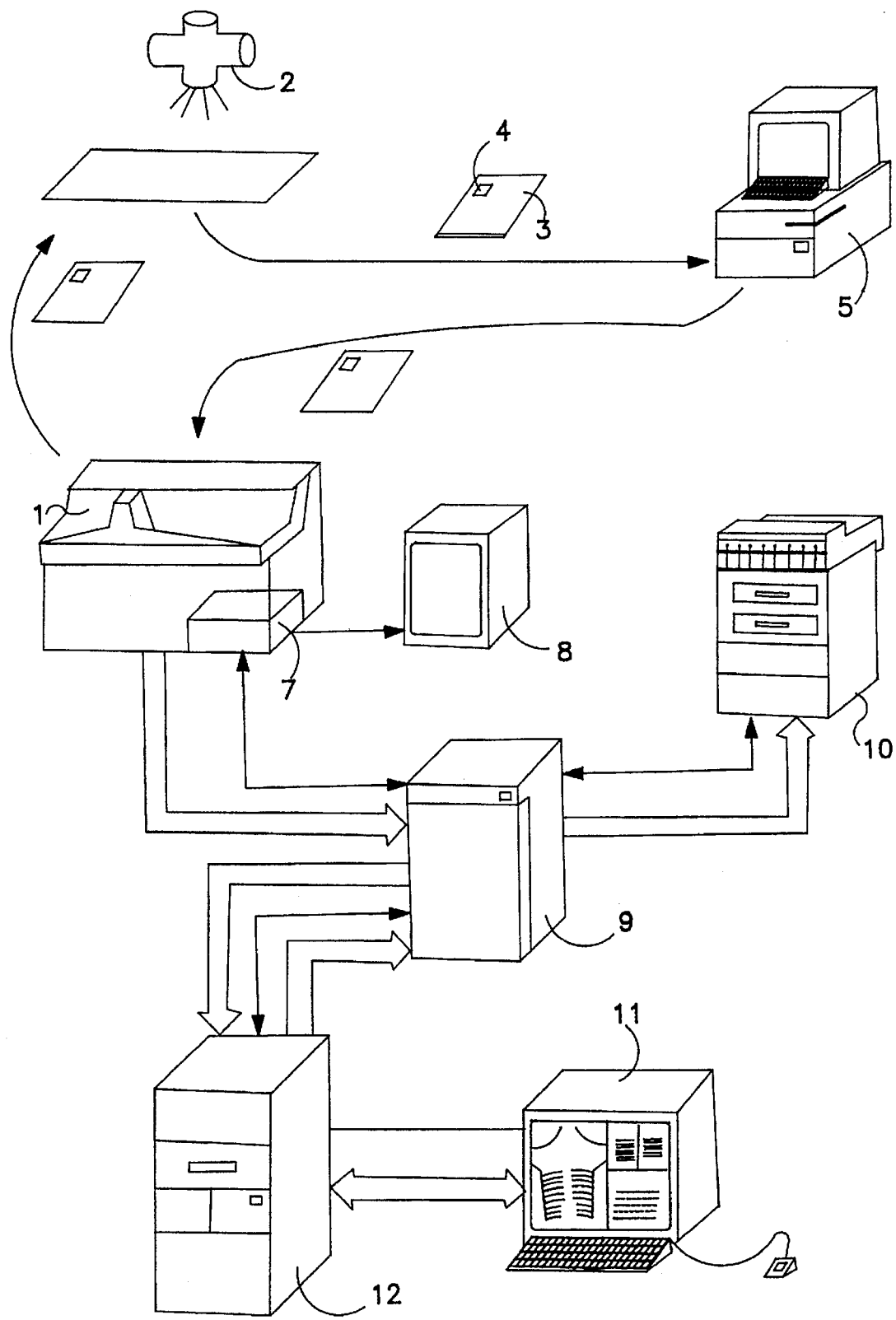
FIG. 1 is a computed radiography system.

The digital raw image signal 22 was then sent to the image processing module of the read-out apparatus (FIG. 1, numeral 7) where it was stored in an internal buffer. The image was also sent to a preview monitor, indicated by numeral 8 in FIG. 1, which gave a first impression of the acquired image and hence provided early feedback to the operator in case the acquisition went wrong.

In the on-line processing module of the read-out apparatus the digital image signal was subjected to a contrast enhancing image processing method has been described extensively in European patent application 527 525.

The original image was first decomposed into a sequence of detail images at multiple resolution levels and a residual image at a resolution level lower than the minimum of said multiple resolution levels, the number of pixels in each detail image decreasing at each coarser resolution level.

Then the pixel values of said detail images were modified to yield pixel values of a set of modified detail images according to a non-linear monotonically increasing odd conversion function with a slope that gradually decreases with increasing argument values.

Next, a processed image was computed by applying a reconstruction algorithm to the residual image and the modified detail images, the reconstruction algorithm being such that if it were applied to the residual image and the detail images without modification, then said original image or a close approximation thereof would be obtained.

Figure 4:
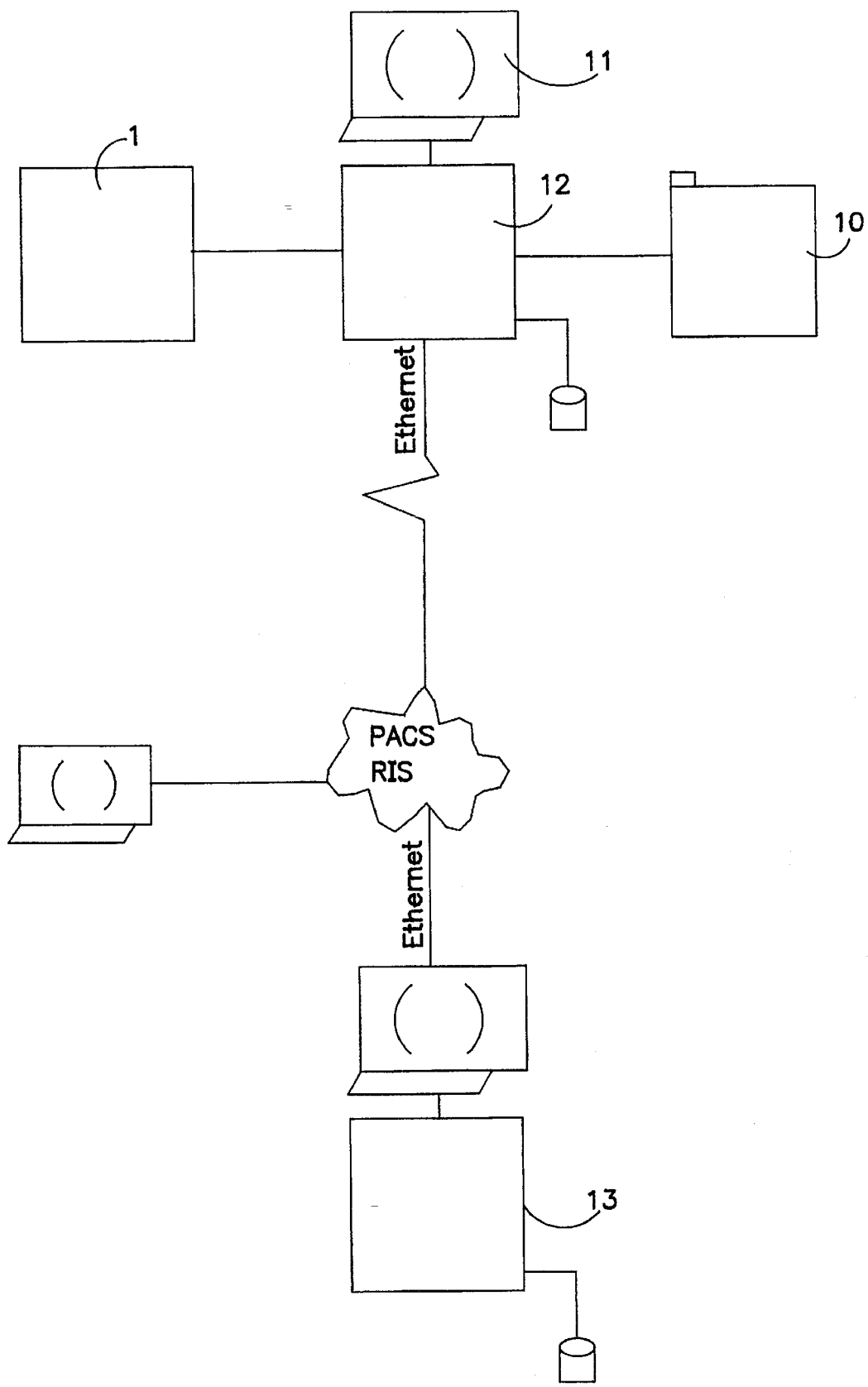
FIG. 4 is an illustration of a remote display station.

The decomposed digital image signal was also sent to an off-line processing station 12 and associated console 11 that was connected via a network with a remote display station as will be explained further on and as is illustrated in FIG. 4.

The processing station used in this embodiment was a SUN SPARC station 630.

The system was also connected to a laser imager 10 to print the images on high quality laser film.

The processing station allows performing a variety of interactive image processing operations such as viewing the digitized image on screen, collimation, zoom etc. In this example the image was subjected to the following image processing actions:

image selection, selection of a specific image processing algorithm on the basis of the radiologist name, the examination type and examination subtype, performing said image processing, contrast enhancement modification, modification of selected window/level, selecting a destination, i.e. a remote station to which the image is transmitted, and corresponding output look up table, modifying spatial and pixel depth resolution, transwriting (i.e. storing) the resulting image (reconstructed up to the required resolution, as has been described higher) on the dedicated NFS partition.

Image processing techniques that can be applied in the processing station have been described in the following patent applications and patents: selection of a diagnostically relevant signal range: EP 549 009, EP 546 600 and European patent application 93 200 376.7; contrast enhancement: EP 527 525 and European patent application 93 200 375.9; noise reduction: European patent application 93 201 432.7; interactive image processing 93 200 374.2; resolution selection: European patent application 93 200 373.4; zooming: European patent application 93 200 377.5.

Figure 3:
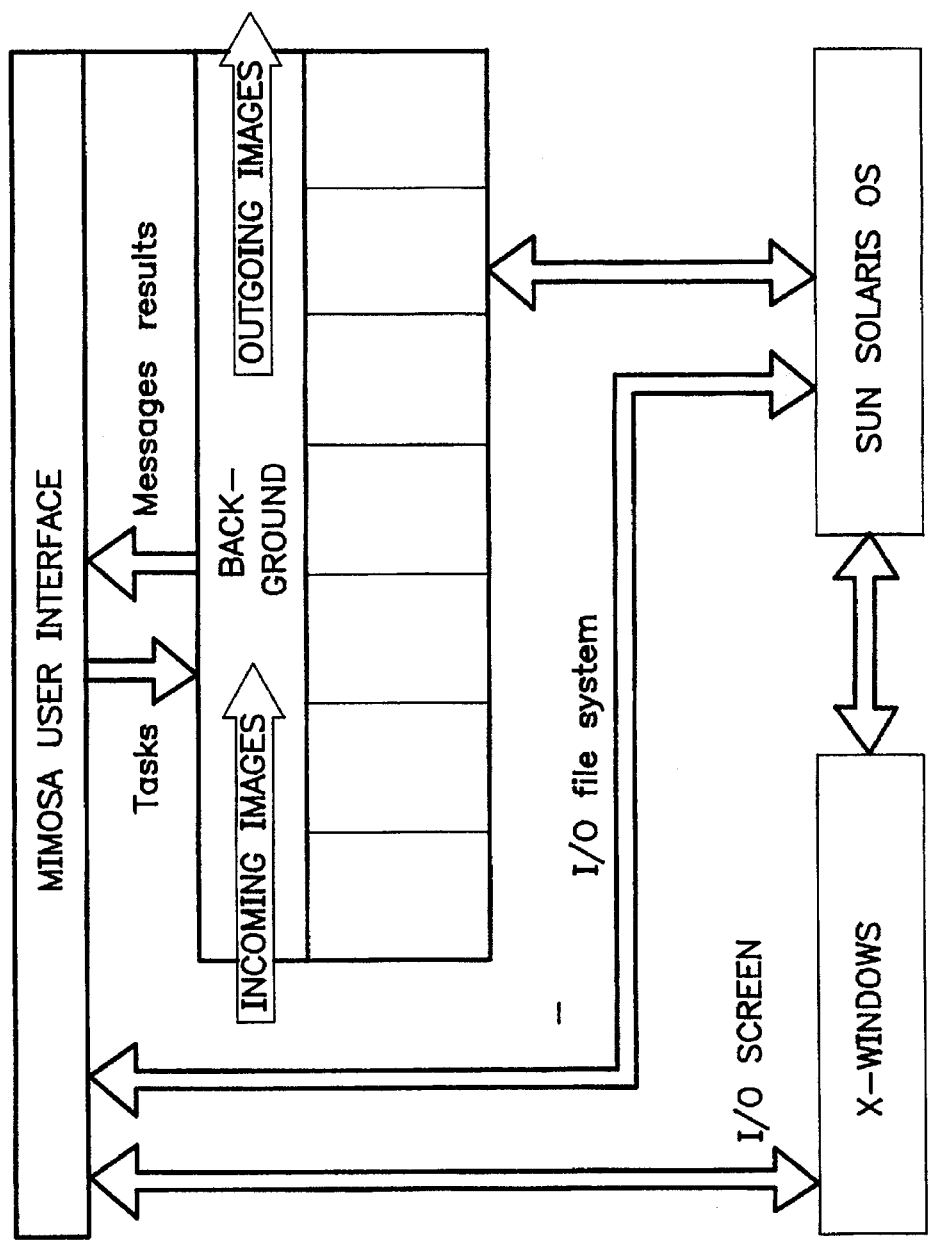
FIG. 3 is an illustration of the software running on the processing station.

The software that runs on the processing station has a layered and modular structure that consists of a so-called foreground and a background. This structure is depicted in FIG. 3.

The foreground is that part of the software the user sees and interacts with. It consists of the following modules. A basic processing module provides an easy means of reprocessing images by changing application data or radiologist data. In addition, it offers image positioning correction features, e.g. flipping and rotating the image, and adjusting signal level and signal window. An advanced processing module provides advanced image processing functionality for scientific and academic purposes such as selecting the sensitometric curve, adjusting for collimation, detailed selection of image processing parameters etc. A third module is a system administration module that gives general information about the processing station.

The background, on the other hand, has the following tasks: managing the disk system, checking data base consistency, receiving and processing incoming images from the user interface and finally processing and transmitting outgoing images for hard- or soft-copy or archiving.

The foreground and background run on top of the operating system, i.e. SUN SOLARIS OS. The user communicates with the operating system through X-window.

Upon selection of an image, changing a parameter or clicking a button, the image processing software translates the task into a task for the background, that also exists of several modules such as queue management, creation of a hard copy etc.

Processing station 11, 12 was connected to a remotely positioned display station via an Ethernet LAN and SUN's NFS distributed file system so as to provide transparent file transfer.

In this example the display station was a SUN SPARC-STATION.

The processing station has read, write and execute access to an NFS disc partition of the display station.

A processed image was saved on an NFS disc partition of the remote display device as a so-called SCP file.

A SCP file format is a binary file format. In order to be able to properly decode the SCP file, decoding means in the display station were fed with information on the scanning order, the word length and the bit mapping.

Each file had a specific and unique ISO 9660 compatible file name in the following format: NR.CUST-ID. This name consists of two parts that are separated from each other by a period. CUST-ID is the identification name of the remote station. The file is in the SCP image format and contains a header and a data part.

The header contains relevant image and patient information. The header consists of nine segments numbered from zero to eight. Each segment is 64 bytes long and the data always starts at 4 byte boundaries. Each segment contains a combination of the following two types of information:

Integer: An integer is 4 bytes long and is stored in a big-endian format. Hence, an integer is 32 bits long and the most significant bit comes first.

String: These are stored in standard C format. The ASCII character NUL is used as 'end' character.

The SCP image format is a binary file format. Binary encoded data can use different byte orders, and, in case of bitmap images, different bit orders as well. So, the scanning order, word length and the bit mapping is to be known in order to be able to properly decode the image.

In the SCP image format, the image is encoded in the form of an array of bytes. This array is organized line by line; the first byte corresponds to the upper left pixel of the image. The total number of bytes in the data part, the number of pixels per image line and the number of lines per image are stored in the header part. To be more specific, segments 0, 1 and 2 of the header contain the image information.

The images are 8 to 12 bits deep. This means that the images can contain up to 4096 levels of grey. The used levels of grey have been optimally processed by the processing unit on the basis of a look up table as mentioned higher.

Creation of the look up table can be done based on the CRT characteristics (measured) including CRT gamma value, relative haze, and maximum density on screen or on an ASCII file as input. This ASCII file contains two integers per line; the first integer is a relative input value (X) and must be strictly increasing, the second is the corresponding relative output value (Y). This ASCII file input is important in cases when the non-linearity does not conform to the simple logarithmic curve expressed by the gamma.

A customer program running in the display station scanned the disc for SCP files. It read their header structure and translated the data.

The customer program stored the demographic data and the image data in a local data base and removed the intermediate SCP file.

We claim:

1. A system for supplying a processed X-ray image from an image transmitting processing station to a remote receiver station, the communication protocol used by said receiver station being unknown to said transmitting station, comprising:

means for acquiring a digital signal representation of said X-ray image, a processing station processing the digital signal representation of said X-ray image and transmitting it to a receiver station, a distributed network system interfacing said transmitting processing station and said receiver station, data interchange means enabling interchange of data between said transmitting processing station and said receiver station connected by said network system, storage means accessible by said data interchange means wherein said processed image is stored as a file, and, means for reading a stored file and for translating the data in the file into a structure to use in an application program running on said remote receiving station.

2. A system according to claim 1 wherein said means for acquiring a digital signal representation comprise:

means for scanning a photostiumulable phosphor screen that has been exposed to a radiation image by means of stimulating radiation, means for detecting light emitted upon stimulation, and, means for converting the detected light into said digital signal representation.

3. A system according to claim 1 wherein said storage means are part of the processing station and has means for copying said processed image from said storage means onto second storage means part of said remote station.

4. A system according to claim 1 wherein said processing station comprises means for storing a look up table representing output characteristics of said remote station and means for applying look up table data to said radiation image.

5. A system according to claim 1 further comprising means for modifying the resolution of said signal representation.

6. A system according to claim 1 further comprising means for modifying the pixel depth of pixels of said digital signal representation.

7. A system according to claim 1 further comprising more than one remote station, each of said stations being identified by means of a destination key, and means to associate one of said destination keys with an image to be supplied to a station and means are provided to transmit an image having a given destination key to the identified remote station.

8. A system according to claim 7 wherein said means are provided to associate a destination key with at least one of the following items: an examination type, examination subtype and identification of a radiologist.

\* \* \* \* \*